United States Patent
Nakanishi

(10) Patent No.: US 9,352,960 B2
(45) Date of Patent: May 31, 2016

(54) METHOD FOR MANUFACTURING CAPACITIVE MICROMACHINED ULTRASONIC TRANSDUCER AND APPARATUS CONFIGURED TO OBTAIN SUBJECT INFORMATION USING THE CAPACITIVE MICROMACHINED ULTRASONIC TRANSDUCER

(71) Applicant: CANON KABUSHIKI KAISHA, Tokyo (JP)

(72) Inventor: Koichiro Nakanishi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 747 days.

(21) Appl. No.: 13/682,640

(22) Filed: Nov. 20, 2012

(65) Prior Publication Data

US 2013/0135971 A1 May 30, 2013

(30) Foreign Application Priority Data

Nov. 28, 2011 (JP) ................................ 2011-259273

(51) Int. Cl.
| | |
|---|---|
| *B81C 1/00* | (2006.01) |
| *B06B 1/00* | (2006.01) |
| *B81B 3/00* | (2006.01) |
| *G01N 29/24* | (2006.01) |
| *B06B 1/02* | (2006.01) |

(52) U.S. Cl.
CPC ........... *B81C 1/00269* (2013.01); *B06B 1/0292* (2013.01); *B81B 3/0027* (2013.01); *G01N 29/2406* (2013.01)

(58) Field of Classification Search
CPC ...................... G01N 29/2406; B81C 1/00269
USPC ......................................................... 367/181
See application file for complete search history.

(56) References Cited

U.S. PATENT DOCUMENTS

| | | | | |
|---|---|---|---|---|
| 4,665,610 | A | * 5/1987 | Barth | ............................... 438/53 |
| 2004/0085858 | A1 | * 5/2004 | Khuri-Yakub et al. | ........ 367/181 |

FOREIGN PATENT DOCUMENTS

| | | |
|---|---|---|
| CN | 101018428 A | 8/2007 |
| CN | 101614655 A | 12/2009 |
| CN | 101662989 A | 3/2010 |
| GB | 2276979 B | 1/1997 |
| JP | 9-186347 A | 7/1997 |
| JP | 2006-516368 A | 6/2006 |
| JP | 2010-035156 A | 2/2010 |
| JP | 2010-194622 A | 9/2010 |

* cited by examiner

*Primary Examiner* — James Hulka
*Assistant Examiner* — John T Nolan
(74) *Attorney, Agent, or Firm* — Canon USA, Inc. IP Division

(57) ABSTRACT

There is provided a method for manufacturing a capacitive micromachined ultrasonic transducer. In this method, a first insulating layer and a vibrating membrane are bonded by heat treatment and a second insulating layer is formed by thermal oxidation in a single heating step, with a cavity provided in the transducer communicating with the outside of the transducer through a communication portion.

16 Claims, 8 Drawing Sheets

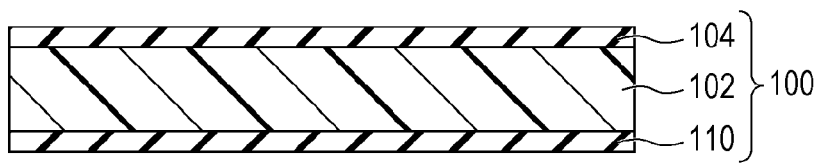
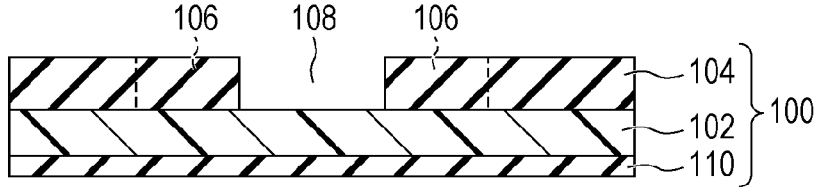
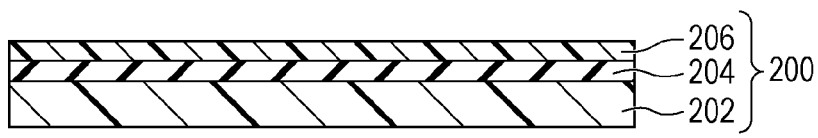
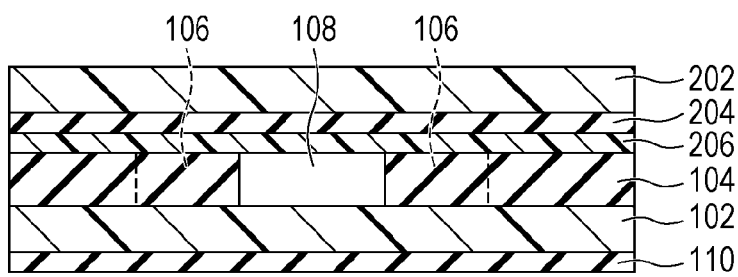
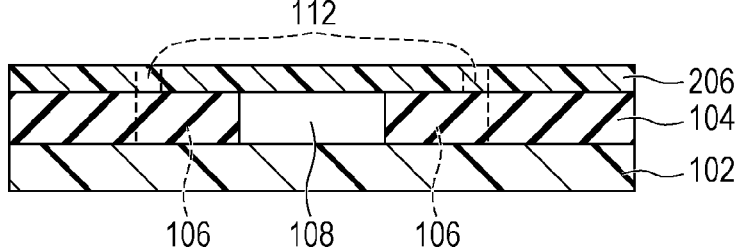
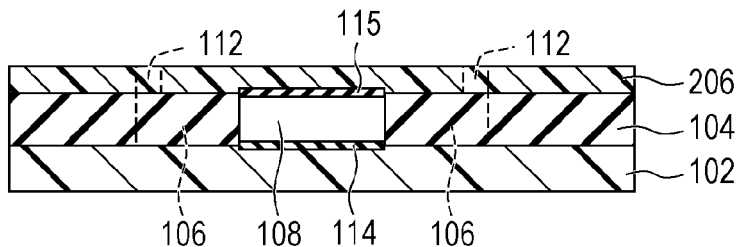
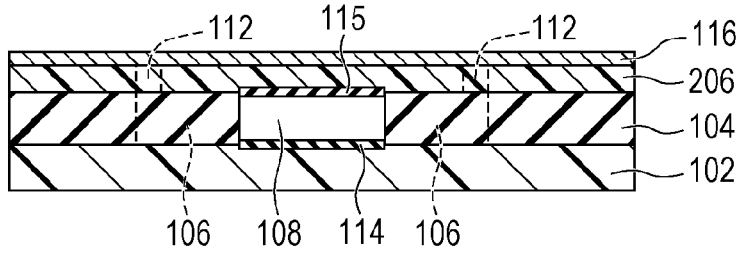

METHOD FOR MANUFACTURING CAPACITIVE MICROMACHINED ULTRASONIC TRANSDUCER AND APPARATUS CONFIGURED TO OBTAIN SUBJECT INFORMATION USING THE CAPACITIVE MICROMACHINED ULTRASONIC TRANSDUCER

BACKGROUND OF THE INVENTION

1. Field of the Invention

The present disclosure relates to a capacitive micromachined ultrasonic transducer that can be used in ultrasonic probes and other applications, and also to a method for manufacturing this capacitive micromachined ultrasonic transducer.

2. Description of the Related Art

Ultrasonic diagnosis has recently been appreciated as a technology for early detection of diseases. In this field of diagnosis, one of the promising ultrasonic transmitting and receiving technologies under research is capacitive micromachined ultrasonic transducers (CMUTs), replacing piezoelectric elements. CMUTs are small and lightweight devices and are fabricated by the rapidly advancing micromachining technology. They have an acoustic impedance similar to that of the human body and thus offer better acoustic impedance matching than known piezoelectric devices. They are also advantageous in many other ways, for example, a broad frequency band in liquids.

PCT Japanese Translation Patent Publication No. 2006-516368 discloses a method for fabricating a CMUT, and this method involves the use of a single-crystal silicon vibrating membrane formed on a silicon substrate by bonding them or other suitable means. More specifically, an oxide film is formed on the silicon substrate by thermal oxidation, the resulting thermal oxide film is partially removed, and then the remaining portion of the thermal oxide film and a piece of single-crystal silicon are bonded. This piece of single-crystal silicon is used as the vibrating membrane, with the space formed by the partial removal of the thermal oxide film as a cavity.

The above patent publication mentions that the manufacturing method disclosed therein may include a second thermal oxidation step. After the removal of the thermal oxide film to expose a portion of the silicon substrate and thereby to form the cavity, the exposed surface of the silicon substrate is thermally oxidized again and thereby coated with an insulating oxide film.

SUMMARY OF THE INVENTION

Aspects of the present disclosure provide CMUTs with improved uniformity in device characteristics and a method for manufacturing such CMUTs.

In the manufacturing method according to an aspect disclosed herein, a first insulating layer and a vibrating membrane are bonded by heat treatment and a second insulating layer is formed by thermal oxidation in a single heating step, with a cavity provided in the CMUT communicating with an outside of the CMUT through a communication portion.

As a result, there are provided CMUTs with improved uniformity in device characteristics and a method for manufacturing such CMUTs.

Further features of the present disclosure will become apparent from the following description of exemplary embodiments with reference to the attached drawings.

BRIEF DESCRIPTION OF THE DRAWINGS

FIGS. 7A to 7G illustrate the manufacturing process of the CMUT described later herein as Example 1.

DESCRIPTION OF THE EMBODIMENTS

The method for manufacturing a CMUT described in PCT Japanese Translation Patent Publication No. 2006-516368 results in poor bonding between the thermal oxide film and single-crystal silicon because the second heating step causes protrusions of the thermal oxide film to form in the bonding interface, although this is not mentioned in the publication. The following describes this situation with reference to FIGS. 9A to 9D.

Figure 9A:
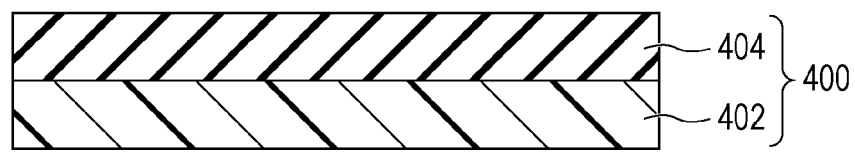
FIGS. 9A to 9D illustrate a known manufacturing process of a CMUT.
Figure 9B:
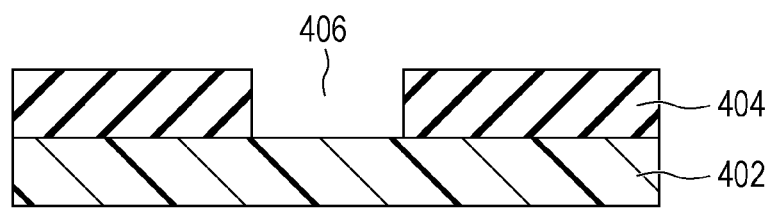
Figure 9C:
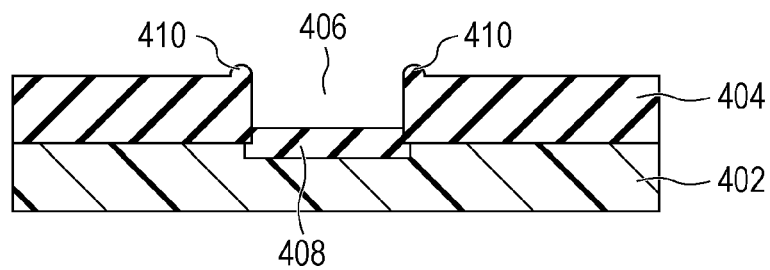
Figure 9D:
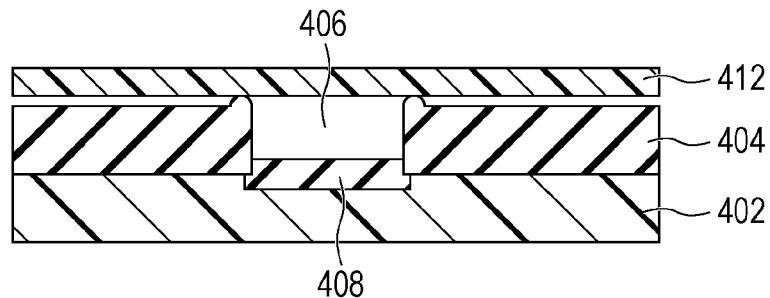

First, as illustrated in FIG. 9A, a silicon (Si) substrate 402 is thermally oxidized (a first heating step) and thereby a base 400 having a silicon oxide film 404 is prepared. Then, as illustrated in FIG. 9B, the silicon oxide film 404 is partially removed by etching and the Si substrate 402 is partially exposed, and thereby a cavity 406 is formed. The surface of the Si substrate 402 exposed to the cavity 406 is thermally oxidized (a second heating step) and thereby a silicon oxide film 408, which serves as an insulator, is formed on the exposed surface of the Si substrate 402. During this second heating step, silicon oxide also accumulates on the exposed bottom portions of the silicon oxide film 404 because these portions are near the cavity 406 and large amounts of oxygen are supplied there. As a result, protrusions 410 are formed on the top of the silicon oxide film 404 as illustrated in FIG. 9C. These protrusions 410 prevent a vibrating membrane 412 from coming into intimate contact as illustrated in FIG. 9D.

Although it is possible to ensure good bonding by removing the protrusions 410 from the interface, this may cause the silicon oxide film 404 to be partially removed together with the protrusions 410. This affects the uniformity of the silicon oxide film 404 and causes the distribution of electric field intensity in the cavity 406 generated upon application of voltage to be uneven. This uneven distribution of electric field intensity leads to varying dielectric breakdown voltages of the resulting CMUT devices and thereby affects the reliability of them.

In light of this, embodiments of the present invention provide methods for manufacturing CMUTs with improved uniformity in device characteristics.

The following describes some embodiments of a method for manufacturing a CMUT according to an aspect of the present disclosure.

Embodiment 1

FIGS. 1A to 1F illustrate a manufacturing process of a CMUT according to this embodiment.

Figure 1A:
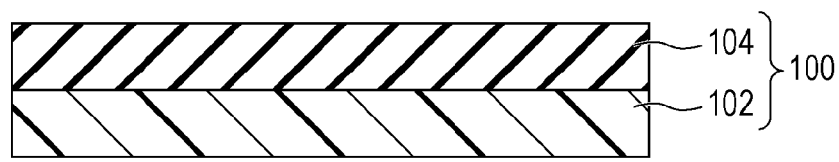
FIGS. 1A to 1F illustrate a manufacturing process of a CMUT according to Embodiment 1.

First, as illustrated in FIG. 1A, a silicon substrate 102 is coated with a first insulating layer 104, which is made of silicon oxide or similar materials, and thereby a base 100 is prepared. The first insulating layer 104 can be formed by thermal oxidation, chemical vapor deposition (CVD), or other suitable techniques. Thermal oxidation can ensure the characteristics of the resulting first insulating layer 104 such as thickness controllability, uniformity, film density, and adhesion to the silicon substrate 102.

Figure 1B:
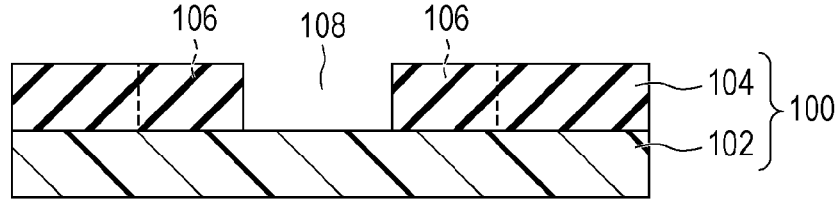

Then, as illustrated in FIG. 1B, the first insulating layer 104 is partially removed and the silicon substrate 102 is partially exposed in a way that the first insulating layer 104 should have a pattern allowing it to support the vibrating membrane and a space that will later serve as a cavity 108 should be formed. A communication passage 106 may also be formed during this step that will later serve as a component of a communication portion that allows the cavity 108 to communicate with the outside.

The height of the space that will later serve as the cavity 108 determines the capacitance and thus should be precisely controlled. The technique used for the partial removal of the first insulating layer 104 should therefore be highly controllable. One example is wet etching with an etchant based on hydrofluoric acid, such as buffered hydrofluoric acid, and this can be used when the first insulating layer 104 is made of silicon oxide. Wet etching with buffered hydrofluoric acid or other hydrofluoric-acid-based etchants, which ensures that the selection ratio between silicon oxide and silicon is almost infinity, allows the height of the cavity 108 to be determined by the thickness of the silicon oxide layer. Reactive ion etching (RIE) and other dry etching techniques can also be used as long as adequate controllability is ensured.

The patterned first insulating layer 104 can also be obtained by using a mask layer so that the first insulating layer 104 can be formed having a predefined pattern. In this case, the mask layer is formed on the silicon substrate 102, the first insulating layer 104 is formed, and then the mask layer is removed, and the step illustrated in FIG. 1A is unnecessary.

Figure 1C:
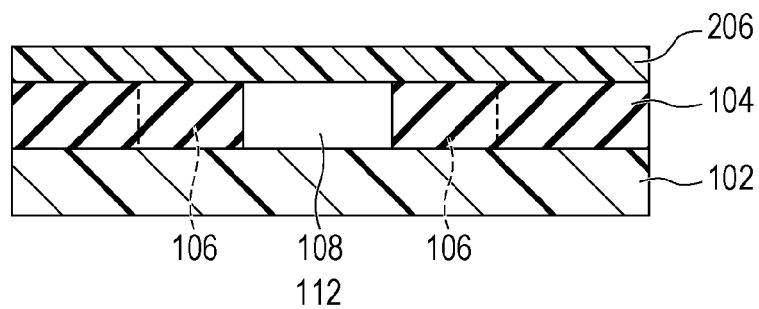

Then, as illustrated in FIG. 1C, a vibrating membrane 206 and the first insulating layer 104 are bonded. The vibrating membrane 206 can be made of a lightweight material with a high Young's modulus, such as single-crystal silicon or silicon nitride. For example, silicon contained in the active layer of a silicon-on-insulator (SOI) substrate can be used for this purpose.

Fusion and other direct bonding techniques ensure sufficient strength of the junction. For example, the vibrating membrane 206 and the first insulating layer 104 can be bonded by overlaying the former on the latter and then heating them.

Figure 1D:
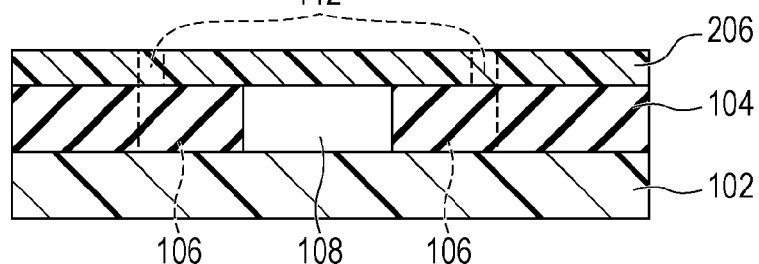

Then, as illustrated in FIG. 1D, communication holes 112 are formed through the vibrating membrane 206 to allow the cavity 108 to communicate with the outside of the transducer. This establishes a communication portion (the communication passage 106 and the communication holes 112) through which the cavity 108 is open to the outside of the CMUT. Although in this embodiment the communication holes 112 are formed through the vibrating membrane 206, the communication holes 112 may be formed through the silicon substrate 102 instead. Furthermore, although in this embodiment the vibrating membrane 206 and the first insulating layer 104 are bonded first and then the communication holes 112 are formed, it is also allowed to form the communication holes 112 through the vibrating membrane 206 first and then bond the vibrating membrane 206 and the first insulating layer 104.

Figure 2A:
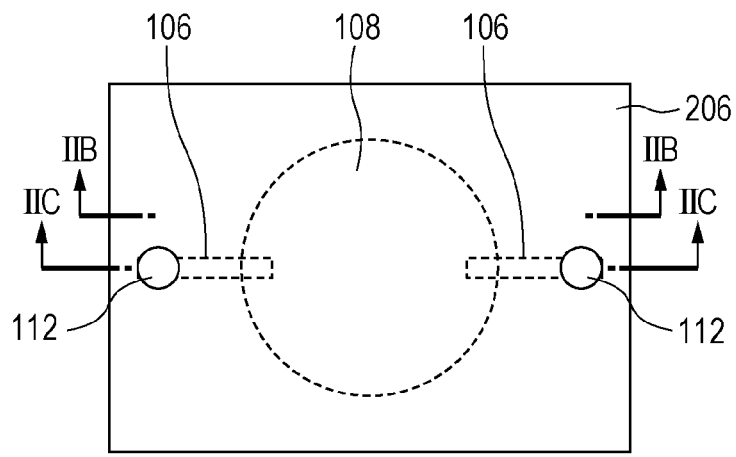
FIGS. 2A to 2C are a plan view and cross-sectional views of the CMUT illustrated in FIG. 1D.
Figure 2B:
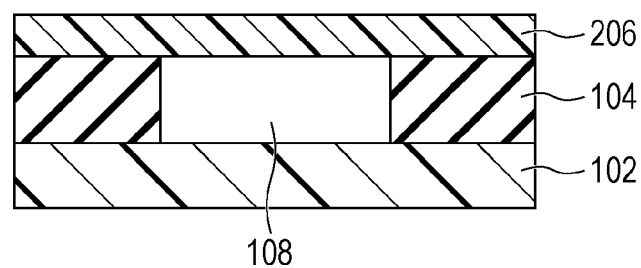
Figure 2C:
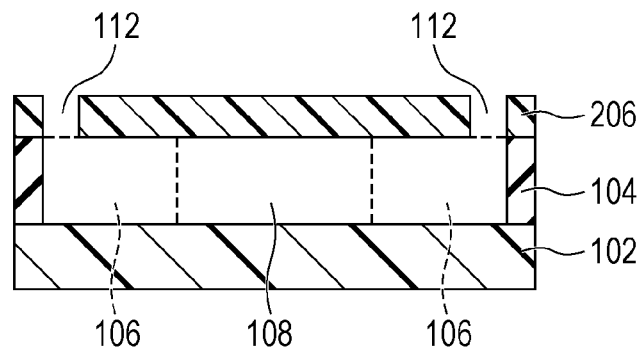

FIG. 2A is a plan view of the CMUT illustrated in FIG. 1D, and FIGS. 2B and 2C are cross-sectional views of the CMUT illustrated in FIG. 2A taken along lines IIB-IIB and IIC-IIC, respectively. As can be seen from FIG. 2C, the cavity 108 can communicate with the outside of the CMUT through the communication portion (the communication passage 106 and the communication holes 112).

Figure 1E:
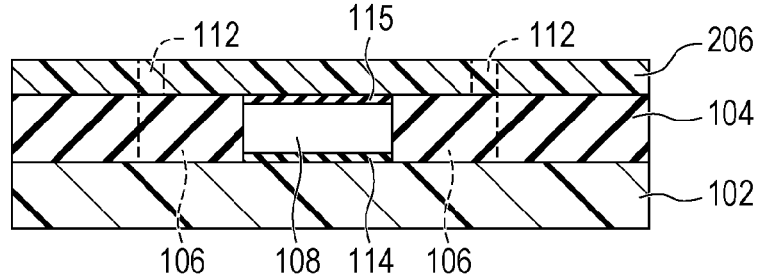

Then, the material(s) for a second insulating layer 114 is introduced in a gaseous form through the communication portion (the communication passage 106 and the communication holes 112), and the second insulating layer 114 is formed in an atmosphere containing the gas in a way that the surface of the silicon substrate 102 exposed to the cavity 108 should be coated as illustrated in FIG. 1E. The second insulating layer 114 can be formed by thermal oxidation, CVD, or other suitable techniques. The formation of the second insulating layer 114 by thermal oxidation includes introduction of oxygen through the communication portion and subsequent heating in the oxygen-containing atmosphere and thus ensures that silicon oxide is incorporated in the resulting insulating layer. CVD allows the second insulating layer 114 to be formed of materials such as silicon nitride. In the case of silicon nitride, the gas introduced as a silicon source can be $SiH_4$, $SiH_2Cl_2$, or the like, and the gas introduced as a nitrogen source can be $N_2$, $NH_3$, or the like.

When the vibrating membrane 206 is made of silicon and thermal oxidation is chosen or when CVD is chosen, another second insulating layer 115 is formed on the surface of the vibrating membrane 206 exposed to the cavity 108. Forming two second insulating layers 114 and 115 on the silicon substrate 102 and the vibrating membrane 206 to coat their surfaces exposed to the cavity 108 in this way can lead to improved insulation between the silicon substrate 102 and the vibrating membrane 206.

Figure 1F:
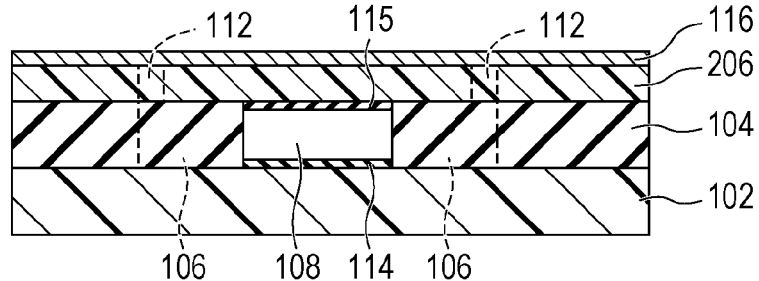
Figure 3:
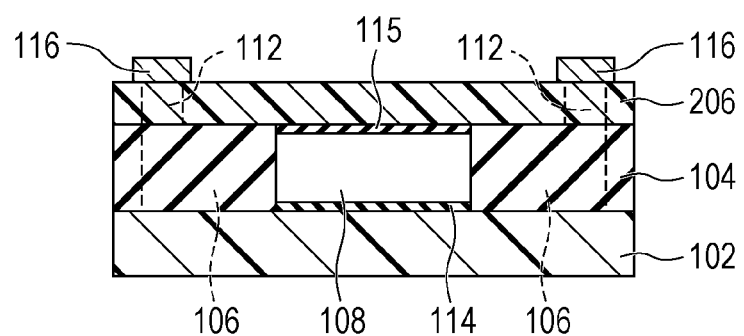
FIG. 3 illustrates a cross-section of another CMUT according to Embodiment 1.

After that, the communication between the cavity 108 and outside the transducer can be blocked; this allows the transducer to be used in liquid or under similar conditions. For example, it is allowed to form a blocking layer 106 configured to seal the communication holes 112 as illustrated in FIG. 1F. The blocking layer 116, if it is used, can be formed from materials such as silicon nitride by CVD or other suitable techniques. In addition to blocking the communication, the blocking layer 116 can be used to modify the mechanical properties of the vibrating membrane 206 as its thickness, stress properties, and other relevant physical characteristics can be appropriately adjusted. It is also allowed to form a blocking layer 116 only to cover the communication holes 112 as illustrated in FIG. 3.

When the vibrating membrane 206 is made of silicon, the communication holes 112 can also be closed by forming an insulating layer on the vibrating membrane 206 to seal the communication holes 112 in parallel with the formation of the second insulating layer 114 in one thermal oxidation step. In this case, the temperature, time, and other conditions of thermal oxidation and the size of the communication holes 112 are selected so as to ensure that the second insulating layer 114 reaches a sufficient thickness before the communication holes 112 are closed.

After the vibrating membrane 206 is placed on the first insulating layer 104, it is allowed to bond the vibrating membrane 206 and the first insulating layer 104 by heat treatment and form the second insulating layer 114 by thermal oxidation in one heating step. A possible way to do this is as follows: the laminate of the first insulating layer 104 and the vibrating layer 206 is heated in a nitrogen-containing atmosphere at 1050° C. for 3 hours and in an oxygen-containing atmosphere at 1050° C. for additional 1 hour. Completing heat bonding and thermal oxidation in one heating step in this way can lead to a simplified manufacturing process of a CMUT with a reduced number of operations.

Completing heat bonding and thermal oxidation in one heating step can also lead to reduced thermal hysteresis of the resulting CMUT. In general, devices with small hysteresis are highly reliable. Completing heat bonding and thermal oxidation in one heating step therefore means improving the manufacturing yield of CMUTs.

Importantly, the communication portion should be open during this heating step for simultaneous heat bonding and thermal oxidation so that the cavity 108 can communicate with the outside of the CMUT.

Figure 4A:
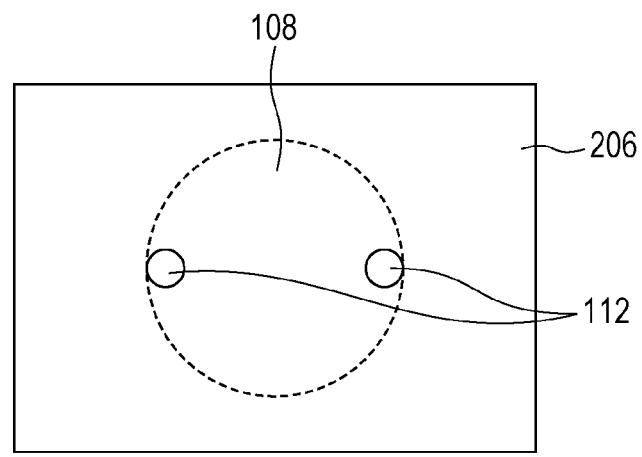
FIGS. 4A and 4B are plan views of the other CMUT according to Embodiment 1.

As illustrated in FIG. 4A, the communication holes 112 may be formed in the portion of the vibrating membrane 206 located above the cavity 108. This arrangement eliminates the need to form the communication passage 106 because the cavity 108 serves as the communication passage 106. In this case, only the communication holes 112 are regarded as the communication portion.

Figure 4B:
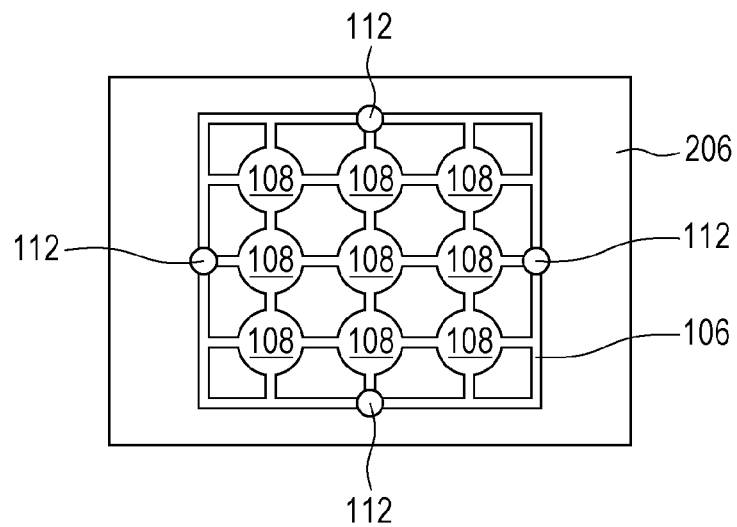

Furthermore, as illustrated in FIG. 4B, it is allowed to form several cavities 108 linked with several communication passages 106. This arrangement leads to a smaller number of communication holes 112 required than is necessary when the cavities 108 are isolated.

In this way, this manufacturing method makes it possible to produce CMUTs with highly uniform device characteristics.
Embodiment 2

Figure 5:
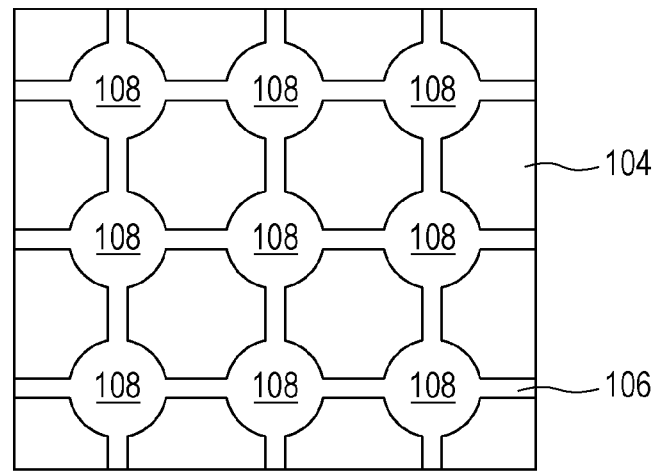
FIG. 5 is a plan view of a first insulating layer configured in accordance with Embodiment 2.

FIG. 5 is a plan view of a patterned first insulating layer 104 configured in accordance with this embodiment. The difference between this embodiment and Embodiment 1 is that in this embodiment no communication holes are formed and the communication portion consists only of communication passages 106 formed during the patterning of the first insulating layer 104. Each communication passage 106 extends from one lateral side of the CMUT to the other side through some cavities 108, allowing the cavities 108 to communicate with the outside of the CMUT.

Figure 6A:
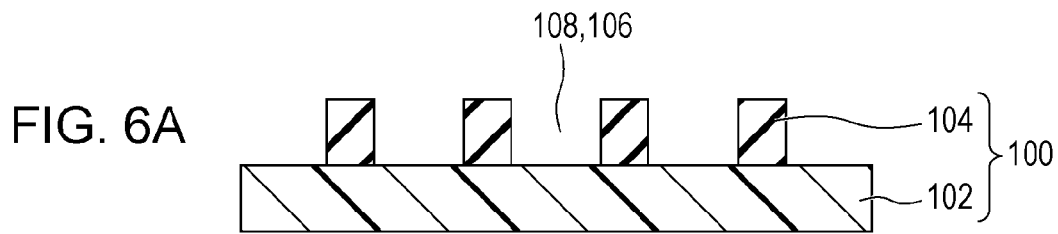
FIGS. 6A to 6C illustrate a manufacturing process of a CMUT according to Embodiment 2.
Figure 6B:
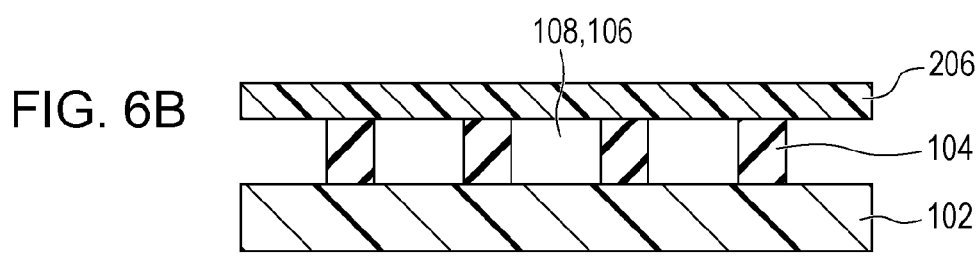
Figure 6C:
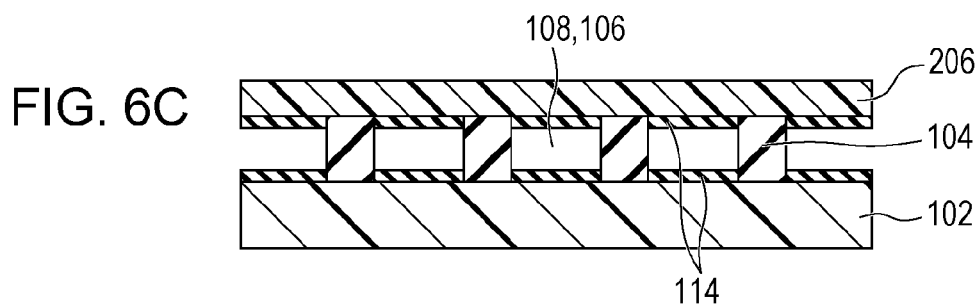

FIGS. 6A to 6C illustrate a manufacturing process of a CMUT according to this embodiment.

First, as illustrated in FIG. 6A, a patterned first insulating layer 104 is formed on a silicon substrate 102. The first insulating layer 104 is patterned in a way that the pattern will later provide the communication passages 106 that ensure communication between the cavities 108 and outside the CMUT. A possible approach to the patterning of the first insulating layer 104 in this way is to form the first insulating layer 104 by thermal oxidation, CVD, or other suitable techniques followed by etching. In another possible approach, the first insulating layer 104 is formed using a mask layer prepared in advance, and then the mask layer is removed.

Then, as illustrated in FIG. 6B, a vibrating membrane 206 and the first insulating layer 104 are bonded.

Through the thus-formed communication portion (the communication passages 106), the material(s) for second insulating layers 114 is introduced in a gaseous form. The second insulating layers 114 are formed in an atmosphere containing the gas in a way that the surfaces exposed to the cavities 108 should be coated as illustrated in FIG. 6C. The second insulating layers 114 can be formed by thermal oxidation, CVD, or other suitable techniques.

After that, the communication between the cavity 108 and outside the transducer can be blocked so that the transducer can be used in liquid or under similar conditions.

In this way, this manufacturing method makes it possible to produce CMUTs with highly uniform device characteristics.

Furthermore, the manufacturing method according to this embodiment, in which no communication holes are formed and the communication portion consists only of communication passages 106 formed during the patterning of the first insulating layer 104, includes a smaller number of operations and is simpler than that according to Embodiment 1.

Forming communication holes as a component of the communication portion through the vibrating membrane 206 as in Embodiment 1 may also cause damage to the vibrating membrane 206. Damage to the vibrating membrane 206 may affect the characteristics of the resulting CMUT.

The method according to this embodiment, however, by which the communication portion can be formed without making communication holes in the vibrating membrane 206, poses reduction of risk for damage to the vibrating membrane 206 associated with the formation of the communication portion.

EXAMPLE 1

The following describes Example 1 of an aspect of the present disclosure with reference to FIGS. 7A to 7G.

First, as illustrated in FIG. 7A, a silicon oxide film 104 is formed on a silicon substrate 102 and thereby a base 100 is prepared. The silicon substrate 102 has a thickness of 300 μm, and its resistance is low (specific resistance ≤0.02 Ω·cm) so that it can be used as the lower electrode. This silicon substrate 102 is thermally oxidized at 1100° C. and thereby the silicon oxide film 104 is formed with a thickness of 200 nm. By this operation, the surface of the silicon substrate 102 opposite to the silicon oxide film 104 is also coated with a silicon oxide film 110.

Then, a resist pattern is formed on the silicon oxide film 104. This resist pattern will later provide a cavity 108 and a communication passage 106 that allows the cavity 108 to communicate with the outside of the transducer. The silicon oxide film 104 is then partially removed by etching with buffered hydrofluoric acid and the silicon substrate 102 is partially exposed in a way that the portions corresponding to the cavity 108 and the communication passage 106 are etched away. After removing the resist pattern, the silicon oxide film 104 is patterned as illustrated in FIG. 7B, with the silicon oxide film 110 covered with a resist so as not to be etched.

Separately, as illustrated in FIG. 7C, another silicon substrate 202 is coated with a silicon oxide layer 204 and then with a silicon film 206 and thereby a SOI base 200 is prepared. The silicon substrate 202 is a 725-μm thick handle layer, the silicon oxide layer 204 is a 400-nm thick buried oxide (BOX) layer, and the silicon film 206 is a 1-μm thick active layer.

Then, as illustrated in FIG. 7D, the silicon film 206 of the SOI base 200 is bonded to the silicon oxide film 104 of the base 100, which has the cavity 108 and the communication passage 106 formed thereon. More specifically, the base 100 and the SOI base 200 are thoroughly washed with sulfuric acid, hydrogen peroxide, hydrochloric acid, and ultrapure water so that their surfaces should be made hydrophilic, and the laminate obtained by simply placing one on the other is heated at 1000° C. for 4 hours. After the completion of this heat bonding step at 1000° C., the silicon handle layer 202 and the silicon oxide BOX layer 204 need to be removed so that the silicon film 206 of the SOI base 200 can be used as the vibrating membrane.

The first step is to make the silicon handle layer 202 as thin as 50 μm by backgrinding. The remaining portion of the silicon handle layer 202 is then removed by etching with a solution of tetramethylammonium hydroxide, with the silicon oxide BOX layer 204 as the etching stop layer and with the silicon oxide film 110 as the etching mask layer for the silicon substrate 102. Subsequently, the silicon oxide BOX layer 204 is removed by etching with buffered hydrofluoric acid. During this operation to remove the silicon oxide BOX layer 204 by etching, the silicon active layer 206 serves as the etching stop layer. The silicon oxide film 110 is also etched away by this operation.

The silicon active layer 206, which will later serve as a vibrating membrane, is exposed in this way. Then, as illustrated in FIG. 7E, communication holes 112 are formed in a way that the cavity 108 can communicate with the outside of the transducer. The communication holes 112 are 6-μm diameter holes formed by patterning using a photoresist and subsequent RIE with a tetrafluoromethane gas and extend through to the communication passage 106.

After removing the unnecessary portion of the photoresist, the entire structure is washed, placed into a thermal oxidation furnace, and thermally oxidized in an oxygen atmosphere at 1000° C. for 2 hours. As a result, the surface of the silicon substrate 102 exposed to the cavity 108 is coated with a thermal oxide film 114 having a thickness of 50 nm as illustrated in FIG. 7F. By this operation, the exposed inner surface of the silicon film 206 is also coated with a silicon oxide layer 115 of a similar thickness.

Then, as illustrated in FIG. 7G, a silicon nitride film 116 is formed on the silicon film 206 by plasma CVD with a thickness of 700 nm to seal the communication holes 112 and to isolate the cavity 108 from outside the transducer.

EXAMPLE 2

The CMUT described in the above example can be applied to apparatuses configured to obtain subject information by means of acoustic waves (hereinafter referred to as acoustic wave analyzers). The acoustic wave analyzer uses CMUTs to receive acoustic waves from a subject and converts the electric signals generated by the CMUTs into pieces of information that indicate the coefficient of optical absorption and other optical properties of the subject, the distribution of acoustic impedance in the subject, and so forth.

Figure 8A:
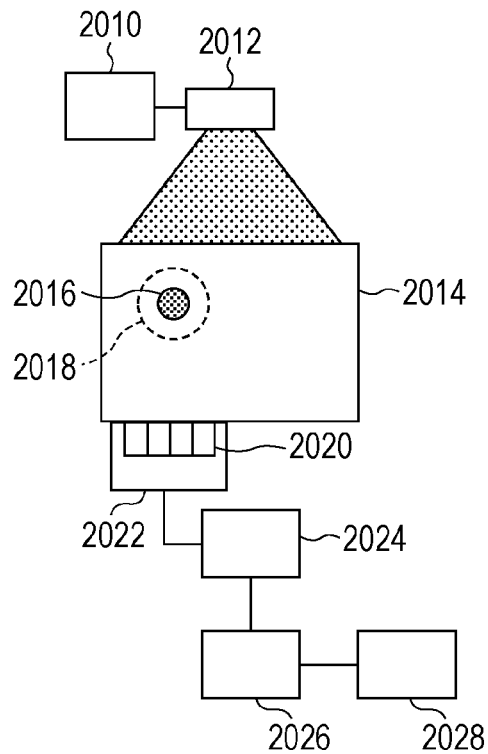
FIGS. 8A and 8B illustrate the composition of apparatuses configured to obtain subject information (hereinafter also referred to as analyzers). These analyzers contain CMUTs as a necessary component and are described later herein as Example 2.

FIG. 8A illustrates the composition of an analyzer that operates on the photoacoustic effect. A light source 2010 generates light pulses, and these light pulses travel through an optical member 2012 composed of lenses, mirrors, fiber optics, and other components and illuminate a subject 2014. The light-absorbing material 2016 existing in the subject 2014 absorbs the energy of the light pulses and emits photoacoustic waves 2018 that behave as acoustic waves. A probe composed of CMUTs 2020 and a housing 2022 receives the photoacoustic waves 2018, transforms them into electric signals, and sends the signals to a signal processor 2024. After processing by the signal processor 2024 including analog-to-digital (A/D) conversion, amplification, and so forth, the electric signals are transmitted to a data processor 2026. The data processor 2026 processes the signals and collects pieces of information about the subject (those indicating the coefficient of optical absorption and other optical properties) in the form of image data. In this example, the signal processor 2024 and the data processor 2026 together operate as a processing unit. A display unit 2028 creates an image from the image data provided by the data processor 2026 and shows the image.

Figure 8B:
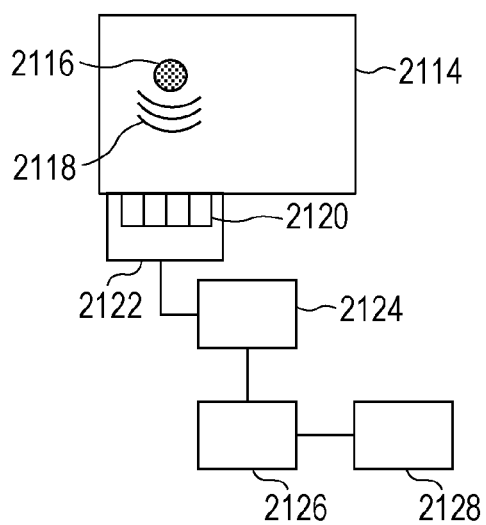

FIG. 8B illustrates the composition of an analyzer that analyzes subjects by means of reflected acoustic waves, e.g., an ultrasonic diagnosis system.

A probe composed of CMUTs 2120 and a housing 2122 emits acoustic waves into a subject 2114, and a portion of the acoustic waves is reflected by a reflective material 2116. The probe in turn receives the reflected acoustic waves 2118 (reflected waves), transforms them into electric signals, and sends the signals to a signal processor 2124. After processing by the signal processor 2124 including A/D conversion, amplification, and so forth, the electric signals are transmitted to a data processor 2126. The data processor 2126 processes the signals and collects pieces of information about the subject (those indicating the distribution of acoustic impedance in the subject) in the form of image data. In this example, the signal processor 2124 and the data processor 2126 together operate as a processing unit. A display unit 2128 creates an image from the image data provided by the data processor 2126 and shows the image.

For both the analyzers illustrated in FIGS. 8A and 8B, the probe may be a scanning unit of mechanical equipment or a hand-held scanner that can be moved manually by the user (a physician, a technician, or the like) on or above the subject. In cases where reflected waves are utilized as in FIG. 8B, the analyzer may incorporate two separate components that serve as an emitter of acoustic waves and a receiver of reflected waves instead of the probe.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-259273 filed Nov. 28, 2011, which is hereby incorporated by reference herein in its entirety.

What is claimed is:

1. A method for manufacturing a capacitive micromachined ultrasonic transducer having a vibrating membrane, a substrate, and a vibrating-membrane-supporting member configured to support the vibrating membrane to form a cavity between the substrate and the vibrating membrane, the method comprising:
   forming a first insulating layer on either side of the substrate, the first insulating layer patterned to serve as the vibrating-membrane-supporting member;
   overlaying the vibrating membrane on the patterned first insulating layer to form the cavity; and
   performing, in a single heating step while the cavity communicates with an outside of the capacitive micromachined ultrasonic transducer through a communication portion that allows the cavity to communicate with an outside of the capacitive micromachined ultrasonic transducer, (i) bonding the first insulating layer and the vibrating membrane by heat treatment after overlaying the vibrating membrane on the patterned first insulating layer, and (ii) forming a second insulating layer on a surface of the substrate or a surface of the vibrating membrane exposed to the cavity by thermal oxidation,
   wherein forming the second insulating layer includes introducing a gas into the cavity through the communication portion and performing subsequent thermal oxidation in an atmosphere containing the gas.

2. The method for manufacturing a capacitive micromachined ultrasonic transducer according to claim 1, wherein the patterned first insulating layer is formed together with a communication passage configured to serve as a component of the communication portion.

3. The method for manufacturing a capacitive micromachined ultrasonic transducer according to claim 2, wherein the communication portion consists only of the communication passage.

4. The method for manufacturing a capacitive micromachined ultrasonic transducer according to claim 1, further comprising providing the substrate or the vibrating membrane with a communication hole configured to function as a component of the communication portion.

5. The method for manufacturing a capacitive micromachined ultrasonic transducer according to claim 1, further comprising forming a blocking layer configured to prevent the cavity from communicating with the outside of the capacitive micromachined ultrasonic transducer after forming the second insulating layer.

6. The method for manufacturing a capacitive micromachined ultrasonic transducer according to claim 1, wherein the substrate is a silicon-containing substrate, and the second insulating layer contains a silicon-oxide-containing layer formed by thermal oxidation of the silicon-containing substrate.

7. The method for manufacturing a capacitive micromachined ultrasonic transducer according to claim 1, wherein the vibrating membrane is a silicon-containing film, and the second insulating layer contains a silicon-oxide-containing layer formed by thermal oxidation of the silicon-containing film.

8. The method for manufacturing a capacitive micromachined ultrasonic transducer according to claim 1, wherein the patterned first insulating layer is formed by forming the first insulating layer on either side of the substrate by thermal oxidation in an atmosphere containing oxygen and subsequent etching on the first insulating layer.

9. The method for manufacturing a capacitive micromachined ultrasonic transducer according to claim 1, wherein, between after forming the first insulating layer and before overlaying the vibrating membrane, the method does not include forming an insulating layer by thermal oxidation of a surface of the substrate in contact with the cavity.

10. The method for manufacturing a capacitive micromachined ultrasonic transducer according to claim 1, further comprising providing the substrate or the vibrating membrane with a communication hole that is configured to allow the cavity to communicate with an outside of the capacitive micromachined ultrasonic transducer and is configured to serve as the communication portion.

11. An apparatus configured to obtain subject information, the apparatus comprising:
a capacitive micromachined ultrasonic transducer produced by a method for manufacturing a capacitive micromachined ultrasonic transducer having a vibrating membrane, a substrate, and a vibrating-membrane-supporting member configured to support the vibrating membrane to form a cavity between the substrate and the vibrating membrane, wherein the method includes:
forming a first insulating layer on either side of the substrate, the first insulating layer patterned to serve as the vibrating-membrane-supporting member,
overlaying the vibrating membrane on the patterned first insulating layer to form the cavity, and
performing, in a single heating step while the cavity communicates with an outside of the capacitive micromachined ultrasonic transducer through a communication portion that allows the cavity to communicate with an outside of the capacitive micromachined ultrasonic transducer, (i) bonding the first insulating layer and the vibrating membrane by heat treatment after overlaying the vibrating membrane on the patterned first insulating layer, and (ii) forming a second insulating layer on a surface of the substrate or a surface of the vibrating membrane exposed to the cavity by thermal oxidation, wherein forming the second insulating layer includes introducing a gas into the cavity through the communication portion and performing subsequent thermal oxidation in an atmosphere containing the gas; and
a processing unit configured to obtain subject information using an electric signal output from the capacitive micromachined ultrasonic transducer, wherein the capacitive micromachined ultrasonic transducer receives an acoustic wave from the subject and transduces the acoustic wave into the electric signal.

12. The apparatus of claim 11, wherein, as a result of the method for manufacturing, a bonding interface between the first insulating layer and the vibrating membrane does not include protrusions of thermal oxide film near the cavity.

13. The apparatus of claim 11, wherein, as a result of the method for manufacturing, a bonding interface between a flat surface of the first insulating layer around the cavity and a flat surface of the vibrating membrane near the cavity are flush with one another.

14. The apparatus of claim 11, wherein the surface of the substrate exposed to the cavity includes a first second-insulating layer and the surface of the vibrating membrane exposed to the cavity includes a second second-insulating layer.

15. The apparatus of claim 14, further comprising a blocking layer, wherein the apparatus includes the first second-insulating layer and the second second-insulating layer before the communication portion is blocked with the blocking layer.

16. A capacitive micromachined ultrasonic transducer produced by a method for manufacturing a capacitive micromachined ultrasonic transducer having a vibrating membrane, a substrate, and a vibrating-membrane-supporting member configured to support the vibrating membrane to form a cavity between the substrate and the vibrating membrane, the method comprising:
forming a first insulating layer on either side of the substrate, the first insulating layer patterned to serve as the vibrating-membrane-supporting member;
overlaying the vibrating membrane on the patterned first insulating layer to form the cavity; and
performing, in a single heating step while the cavity communicates with an outside of the capacitive micromachined ultrasonic transducer through a communication portion that allows the cavity to communicate with an outside of the capacitive micromachined ultrasonic transducer, (i) bonding the first insulating layer and the vibrating membrane by heat treatment after overlaying the vibrating membrane on the patterned first insulating layer, and (ii) forming a second insulating layer on a surface of the substrate or a surface of the vibrating membrane exposed to the cavity by thermal oxidation, wherein forming the second insulating layer includes introducing a gas into the cavity through the communication portion and performing subsequent thermal oxidation in an atmosphere containing the gas.

* * * * *